(12) United States Patent
Matsui

(10) Patent No.: US 8,178,311 B2
(45) Date of Patent: *May 15, 2012

(54) MULTIPLE QUANTIFICATION OF CHOLESTEROL IN LOW DENSITY LIPOPROTEIN

(75) Inventor: Hiroshi Matsui, Niigata (JP)

(73) Assignee: Denka Seiken Co., Ltd., Tokyo (JP)

( * ) Notice: Subject to any disclaimer, the term of this patent is extended or adjusted under 35 U.S.C. 154(b) by 453 days.

This patent is subject to a terminal disclaimer.

(21) Appl. No.: 12/368,051

(22) Filed: Feb. 9, 2009

(65) Prior Publication Data

US 2009/0197288 A1 Aug. 6, 2009

Related U.S. Application Data

(62) Division of application No. 10/537,992, filed as application No. PCT/JP03/15995 on Dec. 12, 2003, now Pat. No. 7,507,551.

(30) Foreign Application Priority Data

Dec. 13, 2002 (JP) ................................. 2002-362970

(51) Int. Cl.
- *C12Q 1/60* (2006.01)
- *C12Q 1/44* (2006.01)
- *C12Q 1/32* (2006.01)
- *G01N 33/92* (2006.01)

(52) U.S. Cl. ................. 435/11; 435/19; 435/26; 436/71

(58) Field of Classification Search ........................ None
See application file for complete search history.

(56) References Cited

U.S. PATENT DOCUMENTS

| | | | |
|---|---|---|---|
| 5,925,534 | A | 7/1999 | Miki et al. |
| 6,194,164 | B1 | 2/2001 | Matsui et al. |
| 6,333,166 | B1 | 12/2001 | Nakamura et al. |
| 6,794,157 | B1 | 9/2004 | Sugiuchi |
| 2002/0015975 | A1 | 2/2002 | Nakamura et al. |
| 2003/0129681 | A1 | 7/2003 | Kishi et al. |
| 2004/0126830 | A1 | 7/2004 | Shull et al. |

FOREIGN PATENT DOCUMENTS

| EP | 0 763 741 | 3/1997 |
|---|---|---|
| EP | 0 887 422 | 12/1998 |
| EP | 1 164 376 | 12/2001 |
| EP | 1 197 564 | 4/2002 |

OTHER PUBLICATIONS

International Search Report of PCT/JP03/15995.
Masahiko Okada et al., "Direct Measurement of HDL Cholesterol: Method Eliminating Apolipoprotein E-Rich Particles", Journal of Clinical Laboratory Analysis 15: 223-229 (2001).
Y. Miki et al., "Homogeneous assay for the selective measurement of LDL-cholesterol with polyanion and amphoteric surfactant", Clinical Chemistry, vol. 45, No. 6, part 2, Jun. 1999, pp. A13, XP001246917 & 51$^{st}$ Annual Meeting of the American Association of Clinical Chemistry; New Orleans, LA, USA; Jul. 25-29, 1999, ISSN: 0009-9147.
Hiroyuki Sugiuchi et al., "Homogeneous assay for measuring low-density lipoprotein cholesterol in serum with triblock copolymer and α-cyclodextrin sulfate", Clinical Chemistry 44:3, 522-531 (1998).
Harry H. Yu et al., "Direct Measurement of LDL-C in Children: Performance of Two Surfactant-Based Methods in a General Pediatric Population", Clinical Biochemistry, vol. 33, No. 2, 89-95, 2000.
Non-Final Office Action U.S. Appl. No. 10/537,992 dated Mar. 3, 2006.
Final Office Action U.S. Appl. No. 10/537,992 dated Sep. 26, 2006.
Non-Final Office Action U.S. Appl. No. 10/537,992 dated Jun. 18, 2007.
Non-Final Office Action U.S. Appl. No. 10/537,992 dated Feb. 20, 2008.
Notice of Allowance U.S. Appl. No. 10/537,992 dated Nov. 10, 2008.

*Primary Examiner* — Rebecca Prouty
*Assistant Examiner* — Paul Martin
(74) *Attorney, Agent, or Firm* — Stephen A. Bent; Foley & Lardner LLP

(57) ABSTRACT

The present invention is intended to provide a method for simultaneously measuring cholesterol in low density lipoprotein and total cholesterol as test components in blood. Specifically, a method is used for simultaneously measuring cholesterol in low density lipoprotein and total cholesterol in a biological sample, whereby cholesterol in low density lipoprotein and total cholesterol in a biological sample are quantified with a single measurement.

13 Claims, 3 Drawing Sheets

MULTIPLE QUANTIFICATION OF CHOLESTEROL IN LOW DENSITY LIPOPROTEIN

CROSS-REFERENCE TO RELATED PATENT APPLICATIONS

This application is a Divisional Application of U.S. Ser. No. 10/537,992 filed Jun. 9, 2005 which is the U.S. National Stage of PCT/JP2003/015995 filed Dec. 12, 2003, and issued as Pat. No. 7,507,551, which claims priority from Japanese Application No. 2002-362970 filed Dec. 13, 2002, each of which is incorporated herein by reference in its entirety.

TECHNICAL FIELD

The present invention relates to a method for simultaneously measuring cholesterol in low density lipoprotein and total cholesterol as test components in blood.

BACKGROUND ART

Low density lipoprotein (hereinafter, referred to as "LDL") plays a major role in cholesterol transportation in blood. In particular, most cholesterol deposited on blood vessel walls in the case of atherosclerosis is derived from LDL. An increase in the amount of LDL cholesterol is one of the major risk factors of arteriosclerotic diseases. Thus separate quantification of LDL cholesterol is clinically useful. Moreover, total cholesterol measurement involves measuring cholesterol in all lipoproteins such as chylomicron (CM), very low density lipoprotein (VLDL), LDL, and high density lipoprotein (HDL). Total cholesterol measurement is still a major lipid test.

Conventional methods for quantifying LDL cholesterol include a method comprising two operations (fractionation and cholesterol quantification) and a calculation method using Friedewald's equation based on total cholesterol, HDL cholesterol, and triglyceride levels.

Fractionation includes an ultracentrifugation method, a precipitation method, an immunological method, and the like. These methods require centrifugation or filtration of samples, so that they are currently hardly spread in the field of clinical examination, in light of convenience and economy. Moreover, the calculation method that involves Friedewald's equation is also problematic in terms of accuracy because it does not take individual variability into consideration and the use thereof is limited.

However, recently, a method for quantifying LDL cholesterol that does not require fractionation, has been reported (JP Patent Publication (Kokai) No. 11-318496 A (1999)). This is currently applied for a reagent for clinical examination in the field of examination. This method comprises a first step of selectively erasing cholesterol in lipoproteins other than LDL in a sample (the term "erase" means to decompose ester-type cholesterol and free cholesterol and to make the decomposed products undetectable in a subsequent second step) and a second step of quantifying LDL cholesterol.

However, although the above reagent for measuring LDL cholesterol is a clinically useful, the use of the reagent has not readily become widespread. This is because total cholesterol measurement has been broadly conducted conventionally and LDL cholesterol levels can be obtained by the use of Friedewald's equation. However, as described above, LDL cholesterol levels obtained by the use of Friedewald's equation are problematic. Thus, precise measurement of LDL cholesterol levels has clinical significance. Hence, it has been desired to further improve and diffuse the use of a reagent for measuring LDL cholesterol, which has high clinical significance.

In the meantime, concerning measurement of cholesterol in HDL, a method for continuously measuring cholesterol in HDL and total cholesterol with a single measurement has been reported (M L Sampson et al., Ann Clin Biochem, 37, 479-487, 2000). This method comprises putting a sample in a test tube, measuring HDL cholesterol in the sample using an anti-apoB antibody, disrupting a complex of the anti-apoB antibody and an apoB antibody (HDL cholesterol with the anti-apoB antibody bound thereto) using deoxycholic acid, and then enzymatically measuring the remaining non-HDL cholesterol. The total cholesterol level can be found by totaling values obtained by two instances of measurement. Total cholesterol and HDL cholesterol are conventionally measured broadly in medical checkup and the like. Thus, the ability to measure both cholesterol levels simultaneously is significant.

Patent Document 1
  JP Patent Publication (Kokai) No. 11-318496 A (1999)
Non-Patent Document 1
  M L Sampson et al., Ann Clin Biochem, 37, 479-487, 2000

SUMMARY OF THE INVENTION

An object of the present invention is to provide a method that enables simultaneous quantification of LDL cholesterol and total cholesterol with a single measurement. This method is effective as a multiple quantification method whereby quantification values of a plurality of items can be obtained with a single measurement.

We have intensively studied establishment of a system for simultaneously measuring LDL cholesterol and total cholesterol in view of the importance of precise measurement of LDL cholesterol, which is recently attracting attention, and the importance of measurement of total cholesterol, which is conventionally known.

We have enabled simultaneous quantification of LDL cholesterol and total cholesterol with a single measurement by changing a part of the above method for quantifying LDL cholesterol and further using a function for simultaneously analyzing multiple items of an automated analyzer that has been used for clinical and chemical examination; that is, a function whereby a measurement value can be analyzed under different conditions with a single measurement.

Specifically, such a quantification method has made it possible to detect cholesterol in lipoproteins other than LDL in a sample in the first step, which are selectively erased in the first step of the conventional method, and to detect an LDL cholesterol reaction in the second step.

FIG. 1 shows the principle of the method of the present invention. As shown in FIG. 1, the method of the present invention comprises two steps. In the first step, a reaction based on cholesterol in lipoproteins other than LDL in a sample takes place and then a change in absorbance in the reaction solution resulting from the reaction is measured. In the second step, a reaction based on cholesterol in LDL in the sample takes place and then a change in absorbance of the reaction solution resulting from the reaction is measured. The change in absorbance in the second step corresponds to the amount of LDL cholesterol, and the sum of the change in absorbance in the first step and the change in absorbance in the second step corresponds to the change in total cholesterol amount. By varying analytical conditions for measuring such a change in absorbance using an automated analyzer, multiple items can be measured simultaneously with a single measurement. FIG. 1 shows an example of the principle of the measurement method. Specifically, in the first step, a reaction based only on cholesterol in LDL may take place. In the second step, a reaction based on cholesterol in lipoproteins other than LDL may take place.

Under a measurement condition in simultaneous analysis of multiple items using an automated analyzer, LDL cholesterol is quantified by finding the difference between an absorbance obtained by the reaction in the first step and an absorbance obtained by the reaction in the second step, as shown in FIG. 1. Specifically, such a difference is obtained by subtracting an absorbance obtained by measurement 1 (that is, an absorbance measured in the first step) from an absorbance obtained by measurement 2 (that is, an absorbance measured in the second step).

Under another measurement condition, total cholesterol is quantified by finding the total amount of absorbance (absorbance obtained by measurement 2); that is, the sum of a change in absorbance in the first step and a change in absorbance in the second step.

As described above, the present invention provides a method for simultaneously quantifying LDL cholesterol and total cholesterol in the test components in a biological sample with a single measurement utilizing the function for simultaneously analyzing multiple items of an automated analyzer.

The present invention is as follows.
(1) A method for simultaneously measuring cholesterol in low density lipoprotein and total cholesterol in a biological sample, whereby cholesterol in low density lipoprotein and total cholesterol in a biological sample are quantified with a single measurement.
(2) The method of (1), which comprises a first step of causing a reaction of cholesterol in lipoproteins other than the low density lipoprotein in a biological sample and a second step of causing a reaction of cholesterol in the remaining low density lipoprotein.
(3) The method of (1), whereby a measurement value reflecting the existing amount of cholesterol in lipoproteins other than the low density lipoprotein in a biological sample and a measurement value reflecting the existing amount of cholesterol in the low density lipoprotein are obtained with a single measurement and then the existing amounts of cholesterol in the low density lipoprotein and total cholesterol in the biological sample are simultaneously measured based on the two above values.
(4) The method of (3), which comprises the first step of obtaining a measurement value reflecting the existing amount of cholesterol in lipoproteins other than the low density lipoprotein in a biological sample and a second step of obtaining a measurement value reflecting the existing amount of cholesterol in the remaining low density lipoprotein.
(5) The method of any one of (1) to (4), wherein, in the presence of a surfactant acting on lipoproteins other than the low density lipoprotein, the first step comprises causing cholesterol esterase and cholesterol oxidase to act on lipoproteins other than the low density lipoprotein in a biological sample, converting the generated hydrogen peroxide into a quinone dye, and then measuring the resultant, or comprises causing cholesterol esterase and cholesterol dehydrogenase to act on lipoproteins other than the low density lipoprotein in a biological sample and then measuring the generated NADH (reduced β-nicotinamide adenine dinucleotide).
(6) The method of any one of (1) to (5), wherein the second step comprises, adding a surfactant acting at least on the low density lipoprotein to the reaction product of the first step, causing cholesterol esterase and cholesterol oxidase to act on the remaining low density lipoprotein, converting the generated hydrogen peroxide to the quinone dye, and then measuring the resultant or comprises causing cholesterol esterase and cholesterol dehydrogenase to act on the remaining low density lipoprotein and then measuring the generated NADH (reduced β-nicotinamide adenine dinucleotide).
(7) The method of any one of (1) to (6), whereby analysis is carried out under different measurement conditions with a single measurement using an automated analyzer for clinical and chemical examination.
(8) The method of any one of (1) to (7), whereby cholesterol in low density lipoprotein in blood is quantified by finding the difference between absorbances obtained as measurement values in the first and second steps.
(9) The method of any one of (1) to (8), whereby total cholesterol is quantified by finding total absorbance based on a change in absorbance obtained as a measurement value in the first step and a change in absorbance obtained as a measurement value in the second step.
(10) A reagent composition for simultaneously measuring cholesterol in low density lipoprotein and total cholesterol in a biological sample according to the method of any one of (1) to (6).
(11) The reagent composition of (10), which comprises a surfactant acting on lipoproteins other than the low density lipoprotein, a surfactant acting on at least the low density lipoprotein, cholesterol esterase, and cholesterol oxidase.
(12) The reagent composition of (10), which comprises the surfactant acting on lipoproteins other than the low density lipoprotein, the surfactant acting on at least the low density lipoprotein, cholesterol esterase, and cholesterol dehydrogenase.

The present invention is a method for simultaneously measuring cholesterol in LDL and total cholesterol in a biological sample, whereby cholesterol in LDL and total cholesterol in a biological sample are quantified with a single measurement. Specifically, the method of the present invention comprises a first step in which cholesterol in lipoproteins other than LDL in a biological sample is reacted and a subsequent second step in which cholesterol in the remaining LDL is reacted. For example, the method of the present invention can be carried out by obtaining a measurement value reflecting the existing amount of cholesterol in lipoproteins other than LDL and a measurement value reflecting the existing amount of cholesterol in LDL in a biological sample with a single measurement and then simultaneously measuring the existing amounts of cholesterol in LDL and total cholesterol in the biological sample based on the above two values.

Examples of cholesterol contained in lipoproteins include ester type cholesterol (cholesterol ester) and free cholesterol. In this specification, "cholesterol" alone means both types.

The biological samples subjected to the method of the present invention are samples that may contain lipoproteins such as HDL, LDL, VLDL, or CM. Examples of such biological samples include, but are not limited to, body fluids such as blood, sera, and plasma, and dilutions thereof. "Lipoproteins other than LDL" mean HDL, VLDL, CM, and the like.

"Measurement value reflecting the existing amount of cholesterol in lipoproteins other than LDL" and "measurement value reflecting the existing amount of cholesterol in LDL" mean a value obtained by quantification of the concentration or absolute amount of cholesterol in lipoproteins in a biological sample. Measurement methods for obtaining such a value are not limited. Such a value corresponds to the concentration or absolute amount of cholesterol in lipoproteins in a biological sample, which is finally obtained by a combination of a plurality of methods. For example, such a value may be in proportion to or in inverse proportion to the concentration or absolute amount of cholesterol in lipoproteins in a biological sample. An example of such a measurement value is the absorbance resulting from a compound that is generated by treating cholesterol in lipoproteins with a specific drug. In addition, examples of such a measurement value in this case include both an absolute value and a changed value. For example, a change in absorbance between the first and the second steps as shown in FIG. 1 includes the absorbance elevated in the second step in addition to the absorbance elevated in the first step. This is because the compound generated in the reaction in the first step has the same absorbance wavelength as that of the compound generated in the reaction in the second step. The absorbance wavelength of the compound generated in the reaction in the first step may differ from that of the compound generated in the reaction in the second step. In this case, the absorbance elevated in the second step is not added to the absorbance elevated in the first step and an absorbance measured at another wavelength is elevated from 0 when the second step is initiated. In FIG. 1, an absorbance reflecting the existing amount of cholesterol in lipoproteins other than LDL by measurement 1 in the first step is obtained. This absorbance is "a measurement value reflecting the existing amount of cholesterol in lipoproteins other than LDL." Moreover, in the second step, an absorbance is obtained by measurement 2, which includes the absorbance corresponding to the existing amount of cholesterol in LDL in addition to the absorbance reflecting the existing amount of cholesterol in lipoproteins other than LDL obtained in the first step. This absorbance represents the existing amount of total cholesterol. Furthermore, this absorbance is "a measurement value reflecting the existing amount of cholesterol in LDL" because this includes the absorbance corresponding to the existing amount of cholesterol in LDL in addition to the absorbance obtained in the first step. Furthermore, when addition of such an absorbance is taken into consideration, the "measurement value reflecting the existing amount of cholesterol in LDL" can also be said to be a "measurement value containing a value reflecting the existing amount of cholesterol in LDL." Furthermore, in this case, a change in absorbance corresponding to the existing amount of cholesterol in LDL, which absorbance has been added as described above, is also a "measurement value reflecting the existing amount of cholesterol in LDL." That is, in the second step, only a change in absorbance may be measured in the second step.

In the meantime, when the absorbance wavelength of a compound generated in the first step differs from that of the compound generated in the second step, the absorbance measured in the first step is a "measurement value reflecting the existing amount of cholesterol in lipoproteins other than LDL." The absorbance measured in the second step at a wavelength differing from that in the first step is a "measurement value reflecting the existing amount of cholesterol in LDL."

"A single measurement" used when two types of measurement value are obtained with a single measurement involves a series of treatments ranging from subjecting a biological sample to measurement to obtainment of a necessary plurality of measurement values. Such a single measurement includes plural instances of addition of reagents and acquisition of measurement values. Preferably, such a single measurement is completed in a single measurement tube or well alone.

"Simultaneously obtaining the existing amounts of cholesterol in LDL and total cholesterol in a biological sample based on the two measurement values" means to obtain the concentrations or absolute amounts of cholesterol in LDL and total cholesterol by calculation of the two measurement values. For example, as shown in FIG. 1, the existing amount of total cholesterol can be found based on the measurement value obtained in measurement 2. The existing amount of cholesterol in LDL can be found by subtracting the measurement value obtained in measurement 1 from the measurement value obtained in measurement 2. When the absorbance wavelength of a compound generated in the reaction in the first step differs from that of a compound generated in the reaction in the second step as described above, the existing amount of cholesterol in LDL can be found from the value measured in the second step and the existing amount of total cholesterol can be found by adding the value measured in the first step to the value measured in the second step.

The method of the present invention comprises first and second steps. The first step involves treating cholesterol in lipoproteins other than LDL in a sample, such as HDL, VLDL, and CM, and then finding a measurement value reflecting the existing amount. The subsequent second step involves treating the remaining LDL cholesterol and then finding a measurement value reflecting the existing amount. Here, "treat" means to conduct a reaction chemically, physically, and/or biochemically.

Treatment in the first step means to decompose cholesterol by an enzyme reaction in the presence of a surfactant acting on lipoproteins other than LDL. Decomposition products or generated products resulting from the reaction can be chemically, physically, and/or biochemically measured. "Surfactant acting on" refers to decomposition of lipoproteins and liberation of cholesterol from the lipoproteins.

Specific examples of a method for selectively measuring cholesterol contained in lipoproteins other than LDL (that is, cholesterol contained in HDL, VLDL, CM, and the like) include the following methods.

Specifically, an example of a method involves, in the presence of a surfactant acting on lipoproteins other than LDL, causing cholesterol esterase and cholesterol oxidase to act on their target lipoproteins, converting the generated hydrogen peroxide into colored quinone by an oxidation condensation reaction between 4-amino antipyrine and a phenol- or aniline-based hydrogen donor compound through the use of peroxidase, and then measuring the resultant at a wavelength between 400 nm and 700 nm. The absorbance of colored quinone measured in this case reflects the existing amount of cholesterol in lipoproteins other than LDL in a biological sample. In addition, examples of such an aniline-based hydrogen donor compound among hydrogen donor compounds include N-(2-hydroxy-3-sulfopropyl)-3,5-dimethoxyaniline (HDAOS), N-ethyl-N-sulfopropyl-3-methoxyaniline (ADPS), N-ethyl-N-sulfopropyl aniline (ALPS), N-ethyl-N-sulfopropyl-3,5-dimethoxyaniline (DAPS), N-sulfopropyl-3,5-dimethoxyaniline (HDAPS), N-ethyl-N-sulfopropyl-3,5-dimethylaniline (MAPS), N-ethyl-N-sulfopropyl-3-methylaniline (TOPS), N-ethyl-N-(2-hydroxy-3-sulfopropyl)-3-methoxyaniline (ADOS), N-ethyl-N-(2-hydroxy-3-sulfopropyl) aniline (ALOS), N-ethyl-N-(2-hydroxy-3-sulfopropyl)-3,5-dimethoxyaniline (DAOS), N-ethyl-N-(2-hydroxy-3-sulfopropyl)-3,5-dimethylaniline (MAOS), N-ethyl-N-(2-hydroxy-3-sulfopropyl)-3-methoxyaniline (TOOS), and N-sulfopropyl aniline (HALPS).

Another example of such a method involves causing cholesterol esterase and cholesterol dehydrogenase to act on their target lipoproteins and measuring the generated NADH (reduced β-nicotinamide adenine dinucleotide) at a wavelength of 340 nm. However, the method is not limited thereto. The absorbance of NADH measured in this case reflects the existing amount of cholesterol in lipoproteins other than LDL in a biological sample.

The concentration of cholesterol esterase in the reaction solution in the first step is preferably approximately 0.2 to 2.0 IU/ml. Regarding the origin thereof, cholesterol esterase generated by bacteria of the genus Pseudomonas is effective. Furthermore, the concentration of cholesterol oxidase is preferably approximately 0.1 to 0.7 IU/ml. It is preferable to use cholesterol oxidase derived from bacteria, yeast, or the like. Furthermore, the concentration of peroxidase when hydrogen peroxide is converted into colored quinone is preferably 0.4 to 3.0 IU/ml. The concentration of 4-amino antipyrine is preferably 0.4 to 4.0 mmol/l. The concentration of a phenol- or aniline-based hydrogen donor compound is preferably 0.4 to 2.0 mmol/l.

Furthermore, when NADH other than a quinone dye is measured, the concentration of cholesterol esterase is the same as described above, the concentration of cholesterol dehydrogenase is preferably 0.2 to 1.0 IU/ml, and the concentration of NADH is preferably 2.0 to 5.0 mmol/l.

A preferable example of a surfactant acting on lipoproteins other than LDL, which is used in the first step, is a polyalkylene oxide derivative having an HLB value of 13 or more and 15 or less and preferably 13 or more and 14 or less. Examples of such a derivative include condensation products with higher alcohols, condensation products with higher fatty acids, condensation products with higher fatty acid amides, condensation products with higher alkylamines, condensation products with higher alkylmercaptanes, and condensation products with alkyl phenols. In addition, the method for calculating HLB of surfactants is well known, and is described in, for example, Hiroshi Horiuchi, "New Surfactants," 1986, Sankyo Shuppan.

Preferable specific examples of such a polyalkylene oxide derivative having an HLB value of 13 or more and 15 or less include, but are not limited to, compounds having HLB values of 13 or more and 15 or less, such as polyoxyethylene lauryl ether, polyoxyethylene cetyl ether, polyoxyethylene oleyl ether, polyoxyethylene higher alcohol ether, polyoxyethylene octyl phenyl ether, polyoxyethylene nonylphenyl ether, and polyoxyethylene benzyl phenyl ether.

The concentration of the above surfactant used in the first step may preferably be approximately 0.1 to 10 g/l and more preferably approximately 0.5 to 5.0 g/l.

The first step is preferably carried out in a buffer with a pH ranging from 5 to 9. A preferable buffer is a buffer containing amine, such as tris, triethanolamine, or a Good's buffer. In particular, Bis-Tris, PIPES, MOPSO, BES, HEPES, and POPSO, which are Good's buffers, are preferable. The concentration of such a buffer is preferably approximately 10 to 500 mM.

To suppress the reaction with LDL and to further enhance the reaction with the other lipoproteins in the first step, reaction solutions may contain divalent metal ions. As divalent metal ions, copper ions, iron ions, and magnesium ions can be used. Magnesium ions are particularly preferable. The concentration of a divalent metal ion may preferably be approximately 5 to 200 mM.

Furthermore, lipoprotein lipase may also be added to the reaction solution in the first step. Addition of this enzyme is preferable because it facilitates the reaction of, particularly, cholesterol in VLDL. The concentration of this enzyme in the reaction solution may preferably be approximately 5.0 to 10.0 U/ml.

The reaction temperature in the first step may preferably be approximately 30° C. to 40° C., and 37° C. is most preferable. In addition, the reaction time may be approximately 2 to 10 minutes.

According to the method of the present invention, the first step is carried out in the presence of albumin. Albumin is not particularly limited, as long as it is albumin. Commercial albumin such as serum albumin can be preferably used. The source of albumin is not particularly limited and may be any animals such as humans, cattle, pigs, or horses. In particular, widely employed bovine serum albumin can be preferably used. The concentration of the above albumin in the reaction solution in the first step is preferably 0.1 to 5.0 g/dl and further preferably 0.3 to 3.0 g/dl.

In the subsequent second step, the cholesterol remaining in a test sample is quantified. This may be carried out by, for example, adding a surfactant acting on at least LDL and quantifying hydrogen peroxide generated by the action of cholesterol esterase and cholesterol oxidase added in the first step. Hydrogen peroxide can be quantified by a method that involves converting hydrogen peroxide into colored quinone by an oxidation and condensation reaction between 4-amino antipyrine and a phenol- or aniline-based hydrogen donor compound through the use of peroxidase, and then measuring the resultant at a wavelength between 400 nm and 700 nm. When colored quinone is also generated in the reaction in the first step, the absorbance of colored quinone measured in the second step is an absorbance including the absorbance of colored quinone generated in the first step in addition to the absorbance of colored quinone generated in the reaction in the second step. This absorbance reflects the existing amount of cholesterol in LDL in a biological sample and also represents the existing amount of cholesterol in all lipoproteins in the biological sample. On the other hand, when NADH is generated in the reaction in the first step, the abosorbance of colored quinone is measured at a wavelength differing from that of the absorbance of NADH. Thus, the absorbance of colored quinone generated in the reaction in the second step represents the existing amount of cholesterol in LDL in a biological sample. The sum of the absorbance of colored quinone generated in the reaction in the second step and the absorbance of NADH generated in the reaction in the first step represents the existing amount of total cholesterol in the biological sample. Moreover, cholesterol esterase and cholesterol dehydrogenase are caused to act on their target lipoproteins and the generated NADH (reduced β-nicotinamide adenine dinucleotide) may be measured at a wavelength of 340 nm. When NADH is also generated in the reaction in the first step, the absorbance of NADH measured in the second step includes the absorbance of NADH generated in the reaction in the first step in addition to the absorbance of NADH generated in the reaction in the second step. This absorbance reflects the existing amount of cholesterol in LDL in a biological sample and also represents the existing amount of cholesterol in all lipoproteins in the biological sample. On the other hand, when colored quinone is generated in the reaction in the first step, the absorbance of NADH is measured at a wavelength differing from that of the absorbance of colored quinone. Thus, the absorbance of NADH generated in the reaction in the second step represents the existing amount of cholesterol in LDL in a biological sample. The sum of the absorbance of NADH generated in the reaction in the second step and the absorbance of colored quinone generated in the reaction in the first step represents the existing amount of total cholesterol in the biological sample.

Here, the surfactant acting on at least LDL may be a surfactant that selectively acts only on LDL or may be a surfactant that acts on all lipoproteins.

A preferable example of such a surfactant acting on all lipoproteins is a polyalkylene oxide derivative having an HLB value of 11 or more and less than 13, and preferably 12 or more and less than 13. Examples of such a derivative include condensation products with higher alcohols, condensation products with higher fatty acids, condensation products with higher fatty acid amides, condensation products with higher alkylamines, condensation products with higher alkylmercaptanes, and condensation products with alkyl phenols.

Preferable specific examples of such a polyalkylene oxide derivative having an HLB value of 11 or more and less than 13 include, but are not limited to, compounds having HLB values of 11 or more and less than 13, such as polyoxyethylene lauryl ether, polyoxyethylene cetyl ether, polyoxyethylene oleyl ether, polyoxyethylene higher alcohol ether, polyoxyethylene octyl phenyl ether, and polyoxyethylene nonylphenyl ether.

An example of such a surfactant selectively acting only on LDL is an anion surfactant. Preferable examples of such an anion surfactant used herein include, but are not particularly limited to, anion surfactants having one or more aromatic rings to which one or more $C_4$ to $C_{18}$ linear or branched alkyl groups are bound. Here, aromatic rings may preferably consist of carbon and hydrogen, such as benzene, naphthalene, and diphenyl. The aforementioned aromatic rings having one or more hydrophilic groups such as sulfonate bound thereto are further preferable. Preferable examples of such anion surfactants are as shown in the following formulae (I) to (V).

Chemical formula 1

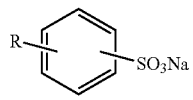
(I)

Chemical formula 2

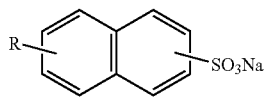
(II)

Chemical formula 3

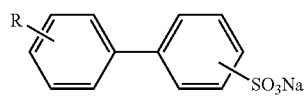
(III)

Chemical formula 4

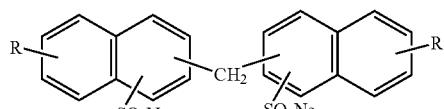
(IV)

Chemical formula 5

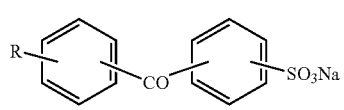
(V)

In formulae (I) to (V), R represents $C_4$ to $C_{18}$ linear or branched alkyl. A preferable example of an anion surfactant used in the second step is higher alcohol sodium sulfate.

The concentration of a surfactant used in the second step is preferably approximately 0.1 to 100 g/l and more preferably approximately 1 to 50 g/l.

Other preferable reaction conditions in the second step are the same as the preferable reaction conditions in the first step.

The first and second steps are carried out successively, preferably within a single reaction chamber. The absorbance upon completion of the first step and the absorbance upon completion of the second step are automatically measured by an automated analyzer.

An analyzer used in the method of the present invention is an automated analyzer having a function for simultaneously analyzing multiple items, by which multiple items can be simultaneously analyzed.

Regarding the function for simultaneously analyzing multiple items of an analyzer, the first to the fourth reagents can be added to a reaction chamber and setting of a reaction time ranging from 3 to 20 minutes is possible. Furthermore, setting of different measuring times is possible because photometry is carried out plural number of instances during reaction time. Thus, setting of different times for calorimetric analysis, rate analysis, or a combination of a colorimetric method and a rate method is also possible. Furthermore, simultaneous measurement at different wavelengths is also possible. Through appropriate setting of these conditions for analysis and measurement, simultaneous measurement of multiple items according to the present invention can be achieved.

A commercial automated analyzer having such a function for simultaneously analyzing multiple items can be used.

The present invention further encompasses a reagent composition that is a kit for simultaneously measuring cholesterol in LDL and total cholesterol in a biological sample. The reagent composition according to the present invention contains a surfactant acting on lipoproteins other than LDL, a surfactant acting on at least LDL, cholesterol esterase, and cholesterol oxidase. Through the use of the reagent composition, the absorbance of colored quinone generated by reaction can be measured. Furthermore, the reagent composition of the present invention contains a surfactant acting on lipoproteins other than LDL, a surfactant acting on at least LDL, cholesterol esterase, and cholesterol dehydrogenase. Through the use of the reagent composition, the absorbance of NADH generated by reaction can be measured. The reagent composition of the present invention further contains a standard lipoprotein solution at a known concentration, a buffer, and the like.

This specification includes part or all of the contents as disclosed in the specification and/or drawings of Japanese Patent Application No. 2002-362970, which is a priority document of the present application.

BEST MODE OF CARRYING OUT THE INVENTION

Specific explanations will be given based on the examples of the present invention. However, the present invention is not limited by the following examples.

(Reagent)

Reagents having the following composition were prepared for simultaneously measuring LDL cholesterol and total cholesterol.

| First reagent | |
|---|---|
| PIPES buffer pH 7.0 | 50 mmol/l |
| HDAOS | 0.7 mmol/l |
| 4-aminoantipyrine | 1.5 mmol/l |
| Cholesterol esterase | 0.8 IU/ml |
| Cholesterol oxidase | 0.5 IU/ml |
| Peroxidase | 1.0 unit/ml |
| Magnesium chloride | 10 mmol/l |
| EMULGEN B66 surfactant (Kao Chemical Company) | 0.2% |
| Second reagent | |
| PIPES buffer pH 7.0 | 50 mmol/l |
| TritonX100 | 3.0% |

As control products to be subjected to evaluation, LDL-EX N reagent for automated analysis (a commercial product produced by DENKA SEIKEN CO., LTD) and T-CHO(S)N reagent for automated analysis (a commercial product produced by DENKA SEIKEN CO., LTD.) were used.

(Sample)

30 samples of human sera were prepared.

TBA-30R (TOSHIBA CORPORATION) was used as an automated analyzer.

(LDL-C and T-CHO reagents for simultaneous measurement (multi-reagent))

Measurement Conditions: Simultaneous Analysis of Multiple Items

300 µl of the first reagent preheated at 37° C. was admixed with 4 µl of each sample, followed by 5 minutes of reaction at 37° C. 100 µl of the second reagent was then added for reaction to take place for 5 minutes, and then the absorbance was measured at 600 nm. LDL cholesterol (LDL-C) measurement was carried out by subtracting the absorbance measured after addition of the first reagent from the absorbance measured after addition of the second reagent. Total cholesterol (T-CHO) measurement was carried out by measuring the absorbance after the addition of the second reagent. Through comparison of these absorbances with the previously measured absorbance of a sample at a known concentration, the concentrations of LDL-C and T-CHO were calculated.

(Control Reagent for Comparison)

Measurement conditions (LDL-C and T-CHO were separately measured under the same conditions)

300 µl of the first reagent preheated at 37° C. was admixed with 4 µl of each sample, followed by 5 minutes of reaction at 37° C. 100 µl of the second reagent was then added for reaction to take place for 5 minutes, and then the absorbance was measured at 600 nm. Measurement was carried out by subtracting the absorbance measured after the addition of the first reagent from the absorbance measured after the addition of the second reagent. Through comparison of these absorbances with the previously measured absorbance of a sample at a known concentration, concentrations were calculated.

Figure 1:
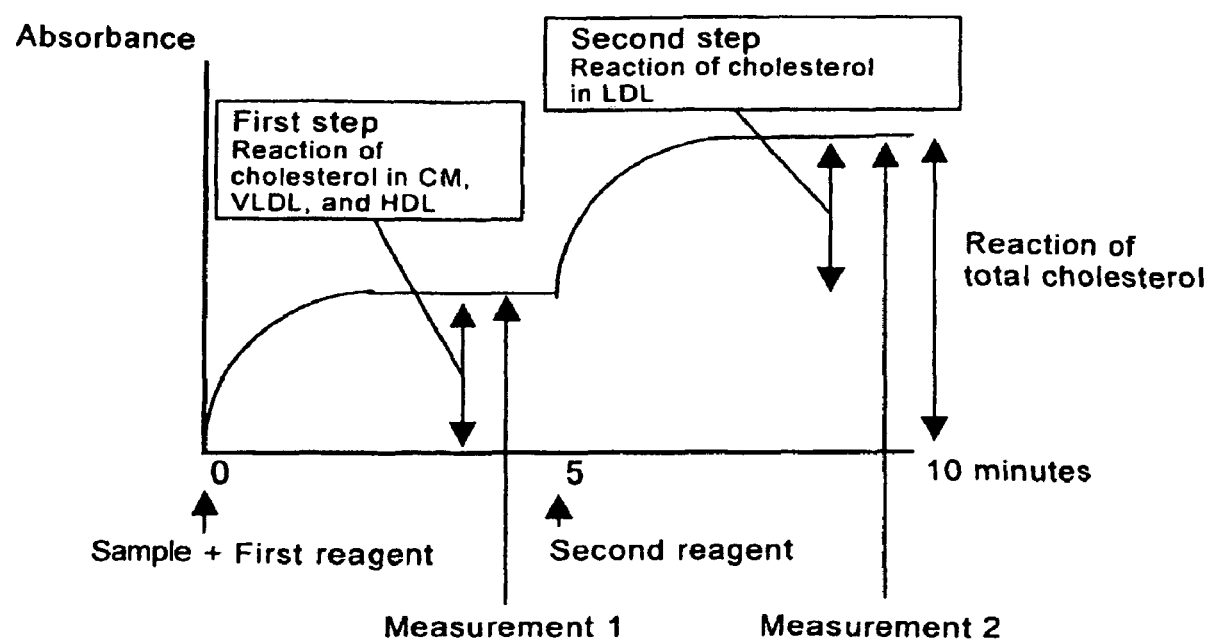
FIG. 1 shows the principle of the multiple quantification method of the present invention.
Figure 2:
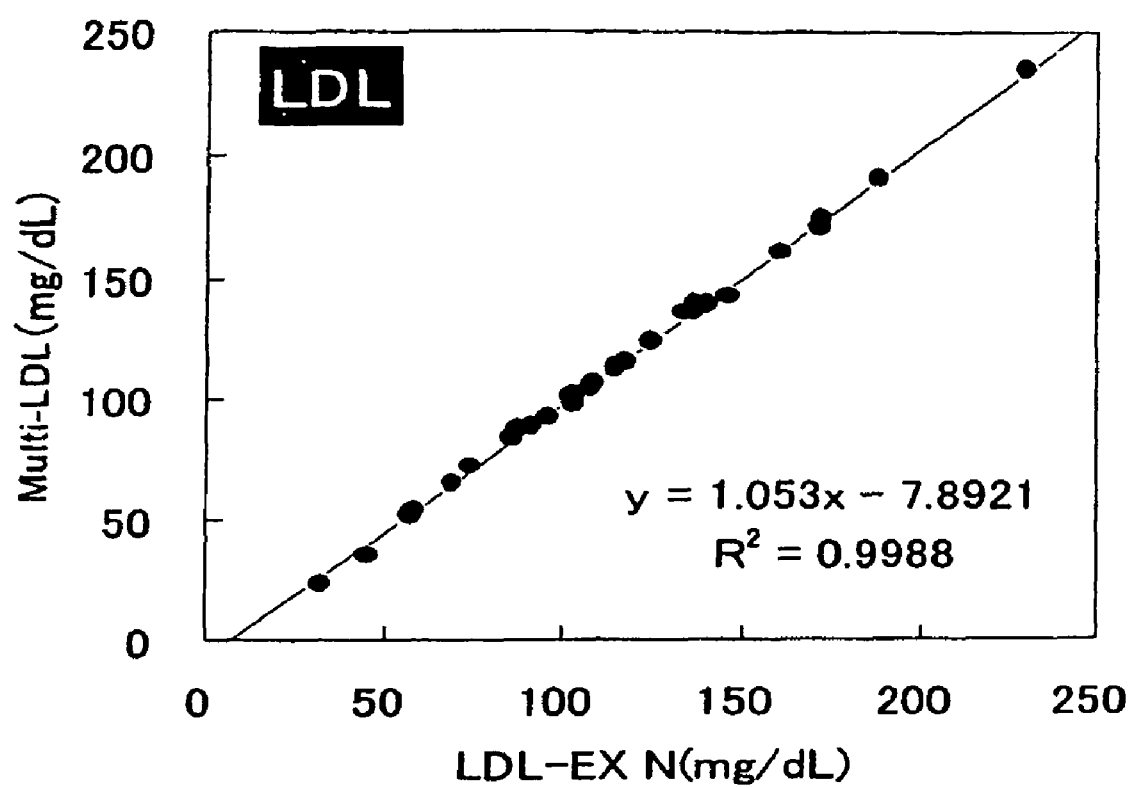
FIG. 2 shows the correlation between cholesterol levels in LDL measured by the multiple quantification method of the present invention and cholesterol levels in LDL measured independently.
Figure 3:
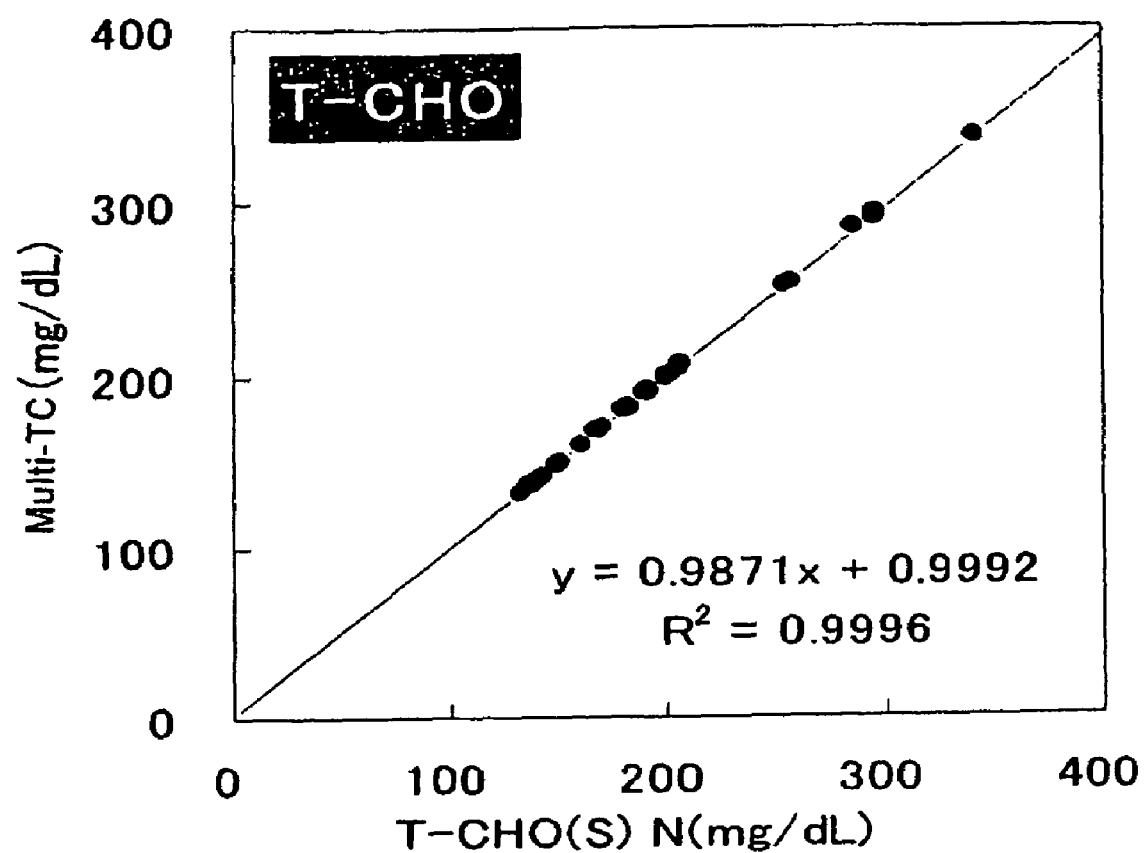
FIG. 3 shows the correlation between total cholesterol levels measured by the multiple quantification method according to the present invention and total cholesterol levels measured independently.

As shown in FIGS. 2 and 3, according to the simultaneous quantification of this method, measurement results similar to those obtained by measuring LDL-C and T-CHO, respectively, were obtained.

All publications, patents, and patent applications cited herein are incorporated herein by reference in their entirety.

Industrial Applicability

The method of the present invention makes it possible to simultaneously quantify LDL cholesterol and total cholesterol with a single measurement.

The invention claimed is:

1. A method for measuring, in one assay, cholesterol in low density lipoprotein and total cholesterol in a biological sample, said method comprising:
   (i) introducing in said sample a first reagent that acts on the cholesterol in lipoproteins other than low density lipoprotein to generate a compound, and then measuring the absorbance of said compound; and subsequently
   (ii) introducing in the same sample from step (i) a second reagent that acts on at least the low density lipoprotein to generate an additional amount of said compound, and then measuring the elevated absorbance of said compound,
   wherein:
   (A) the first reagent has a hydrophile-lipophile balance (HLB) value of between 13 or more and 15 or less and the second reagent has an HLB value of between 12 or more and less than 13; and
   (B) the value from step (i) represents the amount of cholesterol in lipoprotein other than low density lipoprotein, the value from step (ii) represents the amount of total cholesterol in said sample, and the difference in values from step (i) and step (ii) represents the amount of cholesterol in low density lipoprotein.

2. The method of claim 1, wherein said first reagent comprises (i) a surfactant that acts only on lipoproteins other than the low density lipoprotein, (ii) cholesterol esterase, and (iii) cholesterol oxidase.

3. The method of claim 2, wherein said cholesterol esterase is produced by bacteria *Pseudomonas*.

4. The method of claim 2, wherein said first reagent further comprises peroxidase, 4-amino antipyrine and a hydrogen donor compound.

5. The method of claim 4, wherein said hydrogen donor compound is a colored quinone.

6. The method of claim 1, wherein said first reagent comprises (i) a surfactant that acts only on lipoproteins other than the low density lipoprotein, (ii) cholesterol esterase, and (iii) cholesterol dehydrogenase.

7. The method of claim 6, wherein said compound is reduced β-nicotinamide adenine dinucleotide.

8. The method of claim 6, wherein said cholesterol esterase is produced by bacteria *Pseudomonas*.

9. The method of claim 1, wherein said second reagent comprises a surfactant that acts on at least the low density lipoprotein.

10. The method of claim 1, wherein steps (i) and (ii) are carried out in an automated analyzer.

11. The method of claim 1, wherein step (i) is carried out in the presence of albumin.

12. The method of claim 1, wherein step (i) is carried out in the presence of lipoprotein lipase.

13. The method of claim 1, wherein step (i) is carried out in the presence of albumin and lipoprotein lipase.

\* \* \* \* \*